United States Patent [19]

Brady et al.

[11] Patent Number: 4,816,443

[45] Date of Patent: Mar. 28, 1989

[54] PIPTIDES HAVING ANF ACTIVITY

[75] Inventors: Stephen F. Brady, Philadelphia; Ruth F. Nutt, Green Lane, both of Pa.

[73] Assignee: Merck & Co., Inc., Rahway, N.J.

[21] Appl. No.: 51,980

[22] Filed: May 19, 1987

[51] Int. Cl.$^4$ .................. A61K 37/02; C07K 7/08; C07K 7/10
[52] U.S. Cl. ...................... 514/13; 530/326
[58] Field of Search .................. 530/336; 514/13

[56] References Cited

U.S. PATENT DOCUMENTS

| | | | |
|---|---|---|---|
| 4,557,864 | 12/1985 | Needleman | 530/326 |
| 4,607,023 | 8/1986 | Thibault et al. | 530/326 |
| 4,609,725 | 9/1986 | Brady et al. | 530/324 |
| 4,618,600 | 10/1986 | Johnson et al. | 530/326 |
| 4,673,732 | 6/1987 | Kiso et al. | 530/326 |
| 4,716,147 | 12/1987 | Tjoeng et al. | 530/326 |
| 4,721,704 | 1/1988 | Chang et al. | 530/326 |

*Primary Examiner*—Delbert R. Phillips
*Attorney, Agent, or Firm*—Donald J. Perrella; Hesna J. Pfeiffer; Julian S. Levitt

[57] ABSTRACT

Novel peptides having potent natriuretic activity are disclosed with the following amino acid sequence:

Z—(Arg)$_n$—(Arg)$_n$—(DSe or Ser)$_n$—(DSe or Ser)$_n$—Cys—
E—F—G—H—I—J—K—L—M—N—O—P—Q—R—(S)$_n$—Cys—
(T)$_n$—(U)$_n$—(V)$_n$—(DAr or Arg)$_n$—(Tyr)$_n$—Y wherein Z is H, acetyl, Boc or Ser-Leu, E is Phe, NMP, OMT, ChA, F is Gly or DAl, G is Ala or Gly, H is Arg or DAr, Pro, Lys or Dly, I is Ile, Met, MeO, MO$_2$, Leu, Nle, or Val, J is Aib, αMG or αMA, K is Arg or Lys, L is Ile or Val, M is Aib, Gly, Ala or DAl, N is Ala, NMA, Pro, Phe or NMP, O is Gln, DGl, Ala or DAl, P is Ser, His, Arg or Lys, Q is Gly, Pro, Ala or Dal, R is Leu, Phe or ChA, S is Gly, Ala or Dal, Arg or DAr, T is Asn DAs, Ala or Dal, U is Ser, DSe, Ala or DAl, V is Phe, DPh, Ala or DAl, Y is -OH or -NH$_2$ and n is 0 or 1. Also included are the lower alkyl esters and the physiologically acceptable metal salts and acid addition salts of the foregoing peptides. Unless indicated otherwise all optically active amino acids have the L-configuration.

8 Claims, No Drawings

PIPTIDES HAVING ANF ACTIVITY

BACKGROUND OF THE INVENTION

It has been postulated for many years that the cardiac atria serve as sensors that are important in detecting changes in extracellular fluid volume (Gauer et al., Physiol, Rev. 43: 423, 1963). Such a receptor function for the cardiac atria is known in the case of vasopressin, the hypothalmic hormone important in regulating the osmotic concentration of the body fluids.

The postulated existence of a substance which would enhance urinary sodium excretion, and hence be involved in regulation of extracellular fluid volume, was demonstrated recently. de Bold et al., Life Sci. 28: 89, 1981, injected a partially purified extract of cardiac atria of rats into other anesthetized rats and observed a large increase in urine flow and in urinary sodium excretion. This relatively crude extract possessed the appropriate characteristics of an endogenous natriuretic substance.

In addition to its potent diuretic and natriuretic effects, properties that make the material especially appropriate to exert a major effect on body fluid volume regulation, it was also discovered that these extracts of cardiac atria have potent smooth muscle relaxant activity (Currie et al., Science 221: 71, 1983). Such action implies a potential direct role in regulating blood pressure as well as a role in regulating extracellular fluid volume.

Because of the immediately recognized importance of this discovery for understanding the regulation of body fluid volume and blood pressure and the obvious therapeutic potential of such a natural substance in the treatment of congestive heart failure and hypertension, numerous laboratories set about to isolate, characterize and chemically identify the active substance(s) in the cardiac atrial extracts. The active substance(s) in cardiac atria was called atrial natriuretic factor of ANF but has been referred to also as cardionatrin (de Bold et al., Life Sci. 33: 297-302, 1983) and atriopeptin (Currie et al., Science 111: 67, 1984).

DESCRIPTION OF EARLIER ARTICLES AND PATENTS

Thibault et al., FEBS Lett. 164 (2): 286-290 (1983), discloses three peptides of 26, 31 and 33 amino acids and gives their amino acid composition but does not give any amino acid sequences.

Flynn et al., Biochem. Biophys. Res. Comm. 117 (3): 859-865 (1983), discloses a 28-amino acid

```
  6    7    8    9   10   11   12   13   14   15
 Ser—Leu—Arg—Arg—Ser—Ser—Cys—Phe—Gly—Gly—

16   17   18   19   20   21   22   23   24   25
      —Arg—Ile—Asp—Arg—Ile—Gly—Ala—Gln—Ser—Gly—

26   27   28   29   30   31   32   33
                    —Leu—Gly—Cys—Asn—Ser—Phe—Arg—Tyr.
```

There is no suggestion to prepare analogs by substituting amino acids.

Another object is to provide peptides having longer acting ANF activity. Another object is to provide peptides having ANF activity that have improved metabolic stability. These and other objects of the present invention will be apparent from the following description.

SUMMARY OF THE INVENTION

Novel peptides having potent natriuretic activity are disclosed with the following amino acid sequence:

Z—(Arg)$_n$—(Arg)$_n$—(DSe or Ser)$_n$—(DSe or Ser)$_n$—Cys—
E—F—G—H—I—J—K—L—M—N—O—P—Q—R—(S)$_n$—Cys—
(T)$_n$—(U)$_n$—(V)$_n$—(DAr or Arg)$_n$—(Tyr)$_n$—Y wherein Z is H, acetyl, Boc or Ser-Leu, E is Phe, NMP, OMT, ChA, F is Gly or DAl, G is Ala or Gly, H is Arg or DAr, Pro, Lys or Dly, I is Ile, Met, MeO, MO$_2$, Leu, Nle, or Val, J is Aib, αMG or αMA, K is Arg or Lys, L is Ile or Val, M is Aib, Gly, Ala or DAl, N is Ala, NMA, Pro, Phe or NMP, O is Gln, DGl, Ala or DAl, P is Ser, His, Arg or Lys, Q is Gly, Pro, Ala or Dal, R is Leu, Phe or ChA, S is Gly, Ala or Dal, Arg or DAr, T is Asn DAs, Ala or Dal, U is Ser, DSe, Ala or Dal, V is Phe, DPh, Ala or Dal, Y is —OH or —NH$_2$ and n is 0 or 1. Also included are the lower alkyl esters and the physiologically acceptable metal salts and acid addition salts of the foregoing peptides. Unless ndicated otherwise all optically active amino acids have the L-configuration.

DETAILED DESCRIPTION

The peptides of the present invention have activity like that of ANF peptides isolated from biological materials, e.g., potent natriuretic, vasodilatory and hypotensive activity, but have improved metabolic stability which results in longer duration of activity.

In the following description the abbreviations indicated below will be used in place of the corresponding amino acid:

α-MA; α-methylaspartic acid
α-MG; α-methylglutamic acid
Aib; aminoisobutyric acid
Ala; alanine
Arg; arginine
Asn; asparagine
Asp; aspartic acid
ChA; cyclohexylalanine
Dal or D-Ala; D-alanine
DAr or D-Arg; D-arginine
DGl or D-Gln; D-glutamine
DLy or D-Lys; D-lysine
DPh or D-Phe; D-phenylalamine
DSe or D-Ser; D-serine
Gln; glutamine
Glu; glutamic acid
Gly; glycine
His; histidine
Ile; isoleucine
Leu; leucine
Lys; lysine
Met; methionine
MeO; methionine sulfoxide
MO2; methionine sulfone
OMT; O-methyltyrosine (p-methoxyphenylalanine)
NMA; N-methylalanine
Nle; norleucine
Phe; phenylalanine
Pro; proline
Ser; serine
Val; valine
NMP; N-methylphenylalanine

| | Cys — | E — | F — | G — | H — | I — | J — | K — | L — | M — | N — | O — | P — | Q — | R — | S — | Cys |
|---|---|---|---|---|---|---|---|---|---|---|---|---|---|---|---|---|---|
| 1. | Cys | Phe | Gly | Gly | Arg | Ile | Aib | Arg | Ile | Gly | Ala | Gly | Ser | Gly | Leu | — | Cys |
| 2. | " | " | " | " | " | " | " | " | " | " | " | " | " | " | " | Gly | " |
| 3. | " | " | " | " | " | " | MG | " | " | " | " | " | " | " | " | " | " |
| 4. | " | " | " | " | " | " | MA | " | " | " | " | " | " | " | " | " | " |
| 5. | " | OMT | " | " | " | " | Aib | " | " | " | " | " | " | " | " | — | " |
| 6. | " | ChA | " | " | " | " | " | " | " | " | " | " | " | " | " | Gly | " |
| 7. | " | Phe | DAl | " | " | " | " | " | " | " | " | " | " | " | " | " | " |
| 8. | " | " | Gly | DAl | " | " | " | " | " | " | " | " | " | " | " | " | " |
| 9. | " | " | " | Gly | DAr | " | " | " | " | " | " | " | " | " | " | " | " |
| 10. | " | " | " | " | Pro | " | " | " | " | " | " | " | " | " | " | Gly | " |
| 11. | " | " | " | " | Lys | " | " | " | " | " | " | " | " | " | " | " | " |
| 12. | " | " | " | " | DLy | " | " | " | " | " | " | " | " | " | " | " | " |
| 13. | " | " | " | " | Arg | Met | " | " | " | " | " | " | " | " | " | " | " |
| 14. | " | " | " | " | " | MeO | " | " | " | " | " | " | " | " | " | " | " |
| 15. | " | " | " | " | " | MO2 | " | " | " | " | " | " | " | " | " | " | " |
| 16. | " | " | " | " | " | Leu | " | " | " | " | " | " | " | " | " | " | " |
| 17. | " | " | " | " | " | Nle | " | " | " | " | " | " | " | " | " | " | " |
| 18. | " | " | " | " | " | Val | " | " | " | " | " | " | " | " | " | " | " |
| 19. | " | " | " | " | " | Ile | MA | " | " | " | " | " | " | " | " | " | " |
| 20. | " | " | " | " | " | " | MG | " | " | " | " | " | " | " | " | " | " |
| 21. | " | " | " | " | " | " | Aib | Lys | " | " | " | " | " | " | " | " | " |
| 22. | " | " | " | " | " | " | " | Arg | Val | " | " | " | " | " | " | " | " |
| 23. | " | " | " | " | " | " | " | " | Ile | Aib | " | " | " | " | " | " | " |
| 24. | " | " | " | " | " | " | " | " | " | Ala | " | " | " | " | " | " | " |
| 25. | " | " | " | " | " | " | " | " | " | DAla | " | " | " | " | " | " | " |
| 26. | " | " | " | " | " | " | " | " | " | Gly | Glu | " | " | " | " | " | " |
| 27. | " | " | " | " | " | " | " | " | " | " | MAla | " | " | " | " | " | " |
| 28. | " | " | " | " | " | " | " | " | " | " | Phe | " | " | " | " | " | " |
| 29. | " | " | " | " | " | " | " | " | " | " | Pro | " | " | " | " | " | " |
| 30. | " | " | " | " | " | " | " | " | " | " | MPhe | " | " | " | " | " | " |
| 31. | " | " | " | " | " | " | " | " | " | " | Ala | " | " | " | " | " | " |
| 32. | " | " | " | " | " | " | " | " | " | " | " | DGen | " | " | " | " | " |
| 33. | " | " | " | " | " | " | " | " | " | " | " | Ala | " | " | " | " | " |
| 34. | " | " | " | " | " | " | " | " | " | " | " | DAla | " | " | " | " | " |
| 35. | " | " | " | " | " | " | " | " | " | " | " | " | His | " | " | " | " |
| 36. | " | " | " | " | " | " | " | " | " | " | " | " | Arg | " | " | " | " |
| 37. | " | " | " | " | " | " | " | " | " | " | " | " | Lys | " | " | " | " |
| 38. | " | " | " | " | " | " | " | " | " | " | " | " | " | Pro | " | " | " |
| 39. | " | " | " | " | " | " | " | " | " | " | " | " | " | DAl | " | " | " |
| 40. | " | " | " | " | " | " | " | " | " | " | " | " | " | " | " | " | " |
| 41. | " | " | " | " | " | " | " | " | " | " | " | " | " | Ser | Phe | " | " |
| 42. | " | " | " | " | " | " | " | " | " | " | " | " | " | " | ChA | " | " |
| 43. | " | " | " | " | " | " | " | " | " | " | " | " | " | " | Leu | " | " |
| 44. | " | " | " | " | " | " | " | " | " | " | " | " | " | " | " | DAl | " |
| 45. | " | " | " | " | " | " | " | " | " | " | " | " | " | " | " | Ala | " |
| 46. | " | " | " | " | " | " | " | " | " | " | " | " | " | " | " | Arg | " |
| 47. | " | " | " | " | " | " | " | " | " | " | " | " | " | " | " | DAr | " |
| 48. | " | " | " | " | " | " | " | " | " | " | " | " | " | " | " | — | " |

Additional peptides of the present invention are obtained by adding the moieties represented by Z, A, B, C and O to the N-terminus of each of the foregoing peptides. Some examples of these N-terminus additions follow:

| | Z | — A | — B | — C | — D |
|---|---|---|---|---|---|
| 49. | | | | | Ser |
| 50. | | | | Ser | Ser |
| 51. | | | Arg | Ser | Ser |
| | Z | — A | — B | — C | — D |
| 52. | | Arg | Arg | Ser | Ser |
| 53. | Ac | — | — | — | — |
| 54. | Boc | — | — | — | — |
| 55. | Ac | — | — | — | Ser |
| 56. | Boc | — | — | — | Ser |
| 57. | Boc | — | — | Ser | Ser |
| 58. | Ac | — | — | Ser | Ser |
| | Z | — A | — B | — C | — D |
| 59. | Boc | Arg | Arg | Ser | Ser |
| 60. | Ser-Leu | Arg | Arg | Ser | Ser |
| 61. | Ac | Arg | Arg | Ser | Ser |

Other peptides of the present invention are obtained by adding the moieties represented by T, U, V, W, X and Y separately or jointly to the C-terminus of each of the foregoing peptides. Some examples of these C-terminus additions follow:

| T | U | V | W | X |
|---|---|---|---|---|
| Asn | | | | |
| Ala | | | | |
| DAl | | | | |
| Asn | Ser | | | |
| " | DSe | | | |
| " | Ala | | | |
| " | DAl | | | |
| Ala | Ser | | | |
| " | DSe | | | |
| " | Ala | | | |
| " | DAl | | | |
| DAl | Ser | | | |
| " | DSe | | | |
| " | Ala | | | |
| " | DAl | | | |
| Asn | Ser | Phe | | |
| " | " | DPh | | |
| " | " | Ala | | |
| " | " | DAl | | |
| " | DSe | Phe | | |
| " | " | DPh | | |
| " | " | Ala | | |
| " | " | DAl | | |
| " | Ala | Phe | | |
| " | " | DPh | | |

-continued

| T | U | V | W | X |
|---|---|---|---|---|
| Asn | Ala | Ala | | |
| " | " | DAl | | |
| " | DAl | Phe | | |
| " | " | DPh | | |
| " | " | Ala | | |
| " | " | DAl | | |
| Ala | Ser | Phe | | |
| " | " | DPh | | |
| " | " | Ala | | |
| " | " | DAl | | |
| " | DSe | Phe | | |
| " | " | DPh | | |
| " | " | Ala | | |
| " | " | DAl | | |
| " | Ala | Phe | | |
| " | " | DPh | | |
| " | " | Ala | | |
| " | " | DAl | | |
| " | DAl | Phe | | |
| " | " | DPh | | |
| " | " | Ala | | |
| " | " | DAl | | |
| DAl | Ser | Phe | | |
| " | " | DPh | | |
| " | " | Ala | | |
| " | " | DAl | | |
| " | DSe | Phe | | |
| " | " | DPh | | |
| " | " | Ala | | |
| " | " | DAl | | |
| " | Ala | Phe | | |
| " | " | DPh | | |
| " | " | Ala | | |
| " | " | DAl | | |
| DAl | DAl | Phe | | |
| " | " | DPh | | |
| " | " | Ala | | |
| " | " | DAl | | |
| " | " | Ala | | |
| " | " | DAl | | |
| Asn | Ser | Phe | DAl | |
| " | " | DPh | " | |
| " | " | Ala | " | |
| " | " | DAl | " | |
| " | DSe | Phe | " | |
| " | " | DPh | " | |
| " | " | Ala | " | |
| " | " | DAl | " | |
| " | Ala | Phe | " | |
| " | " | DPh | " | |
| " | " | Ala | " | |
| " | " | DAl | " | |
| " | DAl | Phe | " | |
| " | " | DPh | " | |
| " | " | Ala | " | |
| " | " | DAl | " | |
| Ala | Ser | Phe | " | |
| " | " | DPh | " | |
| " | " | Ala | " | |
| " | " | DAl | " | |
| " | DSe | Phe | " | |
| " | " | DPh | " | |
| " | " | Ala | " | |
| " | " | DAl | " | |
| " | Ala | Phe | " | |
| " | " | DPh | " | |
| " | " | Ala | " | |
| " | " | DAl | " | |
| " | DAl | Phe | " | |
| " | " | DPh | " | |
| " | " | Ala | " | |
| " | " | DAl | " | |
| DAl | Ser | Phe | " | |
| " | " | DPh | " | |
| " | " | Ala | " | |
| " | " | DAl | " | |
| " | DSe | Phe | " | |
| " | " | DPh | " | |
| " | " | Ala | " | |
| " | " | DAl | " | |
| " | Ala | Phe | " | |

-continued

| T | U | V | W | X |
|---|---|---|---|---|
| " | " | DPh | " | |
| " | " | Ala | " | |
| " | " | DAl | " | |
| DAl | DAl | Phe | " | |
| " | " | DPh | " | |
| " | " | Ala | " | |
| " | " | DAl | " | |
| Asn | Ser | Phe | DAl | Ty |
| " | " | DPh | " | " |
| " | " | Ala | " | " |
| " | " | DAl | " | " |
| " | DSe | Phe | " | " |
| " | " | DPh | " | " |
| " | " | Ala | " | " |
| " | " | DAl | " | " |
| " | Ala | Phe | " | " |
| " | " | DPh | " | " |
| " | " | Ala | " | " |
| " | " | DAl | " | " |
| " | DAl | Phe | " | " |
| " | " | DPh | " | " |
| " | " | Ala | " | " |
| " | " | DAl | " | " |
| Ala | Ser | Phe | " | " |
| " | " | DPh | " | " |
| " | " | Ala | " | " |
| " | " | DAl | " | " |
| " | DSe | Phe | " | " |
| " | " | DPh | " | " |
| " | " | Ala | " | " |
| " | " | DAl | " | " |
| " | Ala | Phe | " | " |
| " | " | DPh | " | " |
| " | " | Ala | " | " |
| " | " | DAl | " | " |
| " | DAl | Phe | " | " |
| " | " | DPh | " | " |
| " | " | Ala | " | " |
| " | " | DAl | " | " |
| DAl | Ser | Phe | " | " |
| " | " | DPh | " | " |
| " | " | Ala | " | " |
| " | " | DAl | " | " |
| " | DSe | Phe | " | " |
| " | " | DPh | " | " |
| " | " | Ala | " | " |
| " | " | DAl | " | " |
| " | Ala | Phe | " | " |
| " | " | DPh | " | " |
| " | " | Ala | " | " |
| " | " | DAl | " | " |
| " | DAl | Phe | " | " |
| " | " | DPh | " | " |
| " | " | Ala | " | " |
| " | " | DAl | " | " |

The polypeptides of the present invention and the salts thereof can be manufactured according to known synthetic methods elongating the peptide chain, i.e. by condensing amino acids stepwise or coupling the fragments consisting of two to several amino acids, or by combination of both processes, or by solid phase synthesis according to the method originally described by Merrifield, J. Am. Chem. Soc. 85: 2149–2154 (1963). Alternatively, the peptides of the present invention may be synthesized using automated peptide synthesizing equipment.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, N-hydroxysuccinic acid imino ester method, cyanomethyl ester method, etc), Woodward reagent K method, carbonyldiimidazol method, oxidation-reduction method. These condensation reactions may be done in either liquid phase or solid phase. In the case of elongating the peptide chain in the solid phase method, the peptide is attached to an insoluble carrier at the C-terminal amino acid. For insoluble carriers, those which react with the carboxy group of the C-terminal amino acid to form a bond which is readily cleaved later, for example, halomethyl resin such as chloromethyl resin and bromomethyl resin, hydroxymethyl resin, aminomethyl resin, benzhydrylamine resin, and t-alkyloxycarbonylhydrazide resin can be used.

The ANF peptides of the present invention may be prepared from their constituent amino acids by standard methods of protein synthesis, e.g., Schroeder et al., "The Peptides", Vol. I, Academic Press, 1965, or Bodanszky et al., "Peptide Synthesis", Interscience Publishers 1966, or McOmie (ed.), "Protective Groups in Organic Chemistry", Plenum Press 1973, and "The Peptides: Analysis, Synthesis, Biology" 2, Chapter 1 by George Barany and R. B. Merrifield, Academic Press, 1980, N.Y., the disclosures of which are hereby incorporated by reference.

One therapeutic utility of ANF is in congestive heart failure where standard therapy utilizes potent diuretics in combination with peripheral vasodilating drugs. Atrial natriuretic factor combines both of these actions in one molecule which is produced naturally within the body.

In addition to its utility to treat congestive heart failure, a second major therapeutic utility of ANF is essential hypertension. Standard therapy for hypertension utilizes diuretic and peripheral vasodilating drugs. Atrial natriuretic factor incorporates both of these characteristics. A specific use also may be found in the acute treatment of hypertensive crisis such as malignant hypertension where the powerful vasodilating effect of ANF would be paramount.

In addition to these two very broad categories of therapeutic utility, it is possible that those diseases which are characterized by decreases in renal function may benefit because of the favorable action of ANF on renal hemodynamics, especially enhancement of medullary blood flow.

The peptides of the present invention are useful individually or in combination to treat disorders of electrolyte balance and/or altered vascular resistance in a mammalian species, e.g. rats, guinea pigs and sheep, in amount of from about 10 picomoles/kg/min. to about 300 nanomoles/kg/min., preferably from about 100 to about 1000 picomoles/kg/min. The peptides may be administered by intravenous infusion, for example in a suitable physiologically acceptable carrier, e.g., saline or phosphate buffered saline.

The peptides of this invention or their amides, or lower alkyl esters or metal salts or acid addition salts with pharmaceutically acceptable acids are administered to a mammalian species, e.g., rats or mice, systemically, either by intravenous, subcutaneous, or intramuscular injection, or by sublingual or nasal administration, in compositions in conjunction with pharmaceutically acceptable vehicles or carriers. For administration by injection or by the nasal route it is preferred to use the peptides in solution in a sterile aqueous vehicle which may also contain other solutes such as buffers or preservatives as well as sufficient quantities of pharmaceutically acceptable salts or of glucose to make the solution isotonic. In addition, when the above compositions are intended for use as sprays for nasal administration they may also contain small amounts of a pharmaceutically acceptable surface-active agent to ensure rapid absorption of the respective peptide by the nasal mucosa. Examples of such surface-active agents are polysorbate 80 (Tween 80), benzalkonium chloride, bile salts such as sodium glycocholate, dioctyl sodium sulfosuccinate (Aerosol OT), and the like. For sublingual administration it is preferred to formulate the peptides of this invention as rapidly dissolving tablets together with solid excipients or carriers such as lactose. Examples of such excipients or carriers are found in standard pharmaceutical texts, e.g., in Remington's Pharmaceutical Sciences, Mack Publishing Company, Easton, Penn., 1970. Intranasal or sublingual administration may be less precise than intravenous injection but it may be a more convenient form of treatment.

When administration of the peptides of the present invention is desired for the obtention of diuretic, natriuretic, vasorelaxant, hypotensive, or antihypertensive effects such as e.g., in the treatment of hypertension, in particular renovascular hypertension, the dosage to be administered will depend upon such factors as the species, age, weight, sex, and condition of the patient and with the chosen form of administration. Generally, treatment is initiated with small dosages substantially less than the optimum dose of the respective peptide. Thereafter, the dosage is increased by small increments until the optimal effect under the given circumstances is reached. In general, the peptides of this invention are most desirably administered at dosage levels which will give effective concentrations of the respective in the blood of the patient without causing any harmful or deleterious side effects, and preferably at a level that is in the range of from about 0.02 mcg to about 200 mcg per kilogram body weight, although as aforementioned variations will occur. However, for infusion a dosage level that is in the range of from about 0.1 mcg to about 1000 mcg/minute/kg is most desirably employed to achieve effective results. Single doses may be administered in a dosage level of from about 0.01 to about 10 mg in one or more divided doses.

It is often desirable to administer the peptides of this invention continuously over prolonged periods of time n long-acting, slow-release, or depot dosage forms. Such dosage forms may either contain a pharmaceutically acceptable salt of the respective peptide having a low degree of solubility in body fluids, for example one of those salts described above, or they may contain the peptide in the form of a water-soluble salt together with a protective carrier which prevents rapid release. In the latter case, for example, the peptide may be formulated with a non-antigenic partially hydrolyzed gelatin in the form of a viscous liquid; or the peptide may be absorbed on a pharmaceutically acceptable solid carrier, for example zinc hydroxide, and may be administered in suspension in a pharmaceutically acceptable liquid vehicle; or the peptide may be formulated in gels or suspensions with a protective non-antigenic hydrocolloid, for example sodium carboxymethylcellulose, polyvinylpyrrolidone, sodium alginate, gelatin, polygalacturonic acids, for example, pectin, or certain mucopolysaccharides, together with aqueous or nonaqueous pharmaceutically acceptable liquid vehicles, preservatives, or surfactants. Examples of such formulations are found in standard pharmaceutical texts, e.g., in Remington's Pharmaceutical Sciences cited above. Long-acting, slow-release preparations of the peptides of this invention may also be obtained by microencapsulation in a pharmaceutically acceptable coating material, for example gelatin, polyvinyl alcohol or ethyl cellulose. Further examples of coating materials and the processes used for microencapsulation are described by J. A. Herbig in Encyclopedia of Chemical Technology, Vol. 13, 2nd Ed., Wiley, N.Y. 1967, pp. 436–456. Such formulations, as well as suspensions of salts of the peptide which are only sparingly soluble in body fluids, are designed to release from about 0.02 mcg to about 20 mcg of the peptide per kilogram body weight per day, and are preferably administered by intramuscular injection. Alternatively, some of the solid dosage forms listed above, for example certain spargingly water-soluble salts or dispersions in or adsorbates on solid carriers or salts of the peptides, for example dispersions in a neutral hydrogel of a polymer of ethylene glycol methacrylate or similar monomers cross-linked as described in U.S. Pat. No. 3,551,556 may also be formulated in the form of pellets releasing about the same amounts as shown above and may be implanted subcutaneously or intramuscularly.

What is claimed is:

1. A peptide of the formula:

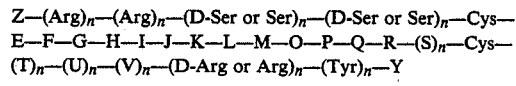

$Z-(Arg)_n-(Arg)_n-(D\text{-Ser or Ser})_n-(D\text{-Ser or Ser})_n-Cys-E-F-G-H-I-J-K-L-M-O-P-Q-R-(S)_n-Cys-(T)_n-(U)_n-(V)_n-(D\text{-Arg or Arg})_n-(Tyr)_n-Y$ wherein Z is H, acetyl, Boc or Ser-Leu, E is Phe, NMP, OMT, ChA, F is Gly or D-Ala, G is Ala or Gly, H is Arg or D-Arg, Pro, Lys or D-Lys, I is Ile, Met, MeO, MO$_2$, Leu, Nle, or Val, J is Aib, αMG or αMA, K is Arg or Lys, L is Ile or Val, M is Aib, Gly, Ala or D-Ala, N is Ala, NMA, Pro, Phe or NMP, O is Gln, D-Gln, Ala or D-Ala, P is Ser, His, Arg or Lys, Q is Gly, Pro, Ala or D-Ala, R is Leu, Phe or ChA, S is Gly, Ala or D-Ala, Arg or D-Arg, T is Asn DAs, Ala or D-Ala, U is Ser, D-Ser, Ala or D-Ala, V is Phe, D-Phe, Ala or D-Ala, Y is —OH or —NH$_2$ and n is 0 or 1, and the lower alkyl esters and the physiologically acceptable metal salts and acid addition salts thereof.

2. A peptide of claim 1 wherein the C-terminal group is —COOH.

3. A peptide of claim 1 wherein the C-terminal group is —CONH$_2$.

4. A peptide of claim 1 in combination with a pharmaceutically acceptable carrier.

5. A method of treating a disorder of electrolyte balance which comprises administering to a mammalian species a therapeutically active amount of a peptide of claim 1.

6. A method of treating a disorder of altered vacular resistance which comprises administering to a mammalian species a therapeutically active amount of a peptide of claim 1.

7. A method of treating essential hypertension which comprises administering to a mammalian species a therapeutically active amount of a peptide of claim 1.

8. A method of treating congestive heart failure which comprises administering to a mammalian species a therapeutically active amount of a peptide of claim 1.

* * * * *

UNITED STATES PATENT AND TRADEMARK OFFICE
CERTIFICATE OF CORRECTION

PATENT NO. : 4,816,443
DATED : March 28, 1989
INVENTOR(S) : Stephen F. Brady and Ruth F. Nutt It is certified that error appears in the above—identified patent and that said Letters Patent is hereby corrected as shown below:

Title page, item [54], and col. 1, line 1, "PIPTIDES" should read "PEPTIDES".

At column 2, line 24, the word reading "ndicated" should read "indicated".

At column 7, line 49, preceding the word "amount" should appear the word "an".

At column 8, line 45, the word " n" should appear the word "in".

At column 9, line 14, the word "spargingly" should appear as the word "sparingly".

In column 10, line 21, in claim 6, the word "vacular" should appear as the word "vascular".

Signed and Sealed this

Twentieth Day of April, 1993

Attest:

MICHAEL K. KIRK

*Attesting Officer*         *Acting Commissioner of Patents and Trademarks*